United States Patent
McBrinn et al.

(10) Patent No.: US 6,716,854 B2
(45) Date of Patent: Apr. 6, 2004

(54) TREATMENTS FOR RESTLESS LEGS SYNDROME

(75) Inventors: Sylvia McBrinn, Stockton, NJ (US); Richard Wayne Anderson, Annandale, NJ (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/423,078

(22) Filed: Apr. 25, 2003

(65) Prior Publication Data

US 2003/0212065 A1 Nov. 13, 2003

Related U.S. Application Data

(62) Division of application No. 10/039,446, filed on Oct. 29, 2001, now Pat. No. 6,602,868.
(60) Provisional application No. 60/244,666, filed on Oct. 31, 2000.

(51) Int. Cl.⁷ ............................................. A61K 31/445
(52) U.S. Cl. .................... 514/317; 514/331; 514/426; 514/428; 514/429
(58) Field of Search ................................ 514/317, 331, 514/429, 426

(56) References Cited

U.S. PATENT DOCUMENTS

| | | | |
|---|---|---|---|
| 5,273,975 A | | 12/1993 | Moon et al. ............. 514/233.2 |
| 5,436,240 A | | 7/1995 | Moon et al. ............. 514/224.5 |
| 5,462,947 A | | 10/1995 | Svensson et al. ........... 514/317 |
| 5,594,024 A | * | 1/1997 | Svensson et al. ........... 514/429 |
| 6,001,861 A | * | 12/1999 | Oertel et al. ................ 514/367 |
| 6,114,326 A | * | 9/2000 | Schueler ..................... 514/220 |

FOREIGN PATENT DOCUMENTS

| | | | | |
|---|---|---|---|---|
| WO | WO 92 18475 | | 10/1992 | |
| WO | WO 99/16442 A | | 4/1999 | ............ A61K/3/00 |
| WO | WO 00 03714 | | 1/2000 | |
| WO | WO 00 40226 A | | 7/2000 | .......... A61K/31/00 |
| WO | WO 01 13903 A | | 3/2001 | .......... A61K/9/20 |
| WO | WO 01/81343 A | | 11/2001 | ......... C07D/471/00 |
| WO | WO 01 83483 A1 | | 11/2001 | ......... C07D/471/06 |

OTHER PUBLICATIONS

SAkipinar, "Restless Legs Syndrome Treatment with Dopaminergic Drugs", Clinical Neuropharmacology, vol. 10, pp. 69–79.

CBrodeur, et al., "Treatment of RLS and PMS with L–dopa: A Double Blinded Control Study", Neurology, 1988, vol. 35, pp. 1845–1848.

KAEkbom, "Restless Legs Syndrome," Neurology, 1960, vol. 10, pp. 868–873.

WAHening, et al., *Dykinesias While Awake and Periodic Movements in Sleep in Restless Legs Syndrome: Treatment with Opioids,* Neurology, 1986 vol. 36, pp. 1363–1366.

JMontplaisir, et al., *"Restless Legs Syndrome and Periodic Movements in Sleep: Physiopathology and Treatment with L–dopa",* Clinical neuropharmacology, 1986, vol. 9, pp. 456–463.

Trzepacz, PT, Violette EJ, Sateia MJ and Hening WA, *"Response to Opioids in Three Patients with Restless Legs Syndrome"*, Am. J. Psychiatry, 1984, vol. 141, pp. 993–99.

CvonScheele, *Levodopa in Restless Legs,* The Lancet, Aug. 23, 1986, pp. 426–27.

ASWalters, et al., *"A Double Blinded Randomized CrossoverTrial of Bromocripitine and Placebo in Restless Leg Syndrome"*, Ann Neurol, 1988, vol. 24, pp. 45–458.

Collado–Seidel V et al., "Aetiology and Treatment of Restless Legs Syndrome" CNS Drugs, ADIA International, Auckland, NZ, vol. 12, No. 1, 1999, pp. 9–20, XP000098933.

Ekesbo, Anna et al., "Effects of the substituted (S)–3–phenylpiperidine (–) Osu6162 on PET Measurements of [11C]SCH2339023390 and [11C] raclopride binding in primate brains" NEUROPHARMACOLOGY (1999), 38 (3), 331–338, XP002200122.

Sethy, Vimala H. et al., "U–95666E: a potential anti–parkinsonian drug with anxiolytic activity" Prog. Neuro–Psychopharmacol. Biol. Psychiatry (1997), 21(5), 873–883, XP002192219, p. 874, paragraph 2, pp. 878, paragraph 2.

Walters A S et al., "A Double–Blind Randomized Crossover Trial of Bromocriptine and Placebo in Restless Legs Syndrome" Annals of Naeurology, Boston, US, vol. 24, No. 3, Sep. 1998, (1988–09), pp. 455–458, XP002117258.

\* cited by examiner

*Primary Examiner*—James H. Reamer
(74) *Attorney, Agent, or Firm*—Peter C. Richardson; Andrea E. Dorigo

(57) ABSTRACT

The invention provides methods and use of heterocyclic amines, and phenylazacycloalkane compounds, and their pharmacologically acceptable salts for the treatment of Restless Legs Syndrome (RLS).

16 Claims, No Drawings

TREATMENTS FOR RESTLESS LEGS SYNDROME

This is a division of U.S. application Ser. No. 10/039,446 filed Oct. 29, 2001 now U.S. Pat. No. 6,602,868, which claims the benefits of U.S. provisional application Ser. No. 60/244,666 filed Oct. 31, 2000 under 35 U.S.C. §119 (e)(1).

FIELD OF THE INVENTION

The present invention relates to methods and use of heterocyclic amines and substituted phenylazacycloalknes, and the pharmaceutically acceptable salts thereof, in the treatment of Restless Legs Syndrome.

BACKGROUND OF THE INVENTION

Restless legs syndrome (RLS) is a neurosensorimotor disorder with parestethesias, sleep disturbances and, in most cases, periodic limb movements of sleep (PLMS).

Two forms of RLS appear to exist: the idiopathic and the uremic form. In this document both forms will be referred to as RLS. RLS is characterized by (1) a desire to move the legs, usually associated with paresthesias/dysesthesias, (2) motor restlessness, (3) worsening or exclusive presence of symptoms at rest (i.e. lying, sitting) with at least partial or temporary relief by activity, and (4) worsening of symptoms during the evening or night. RLS is fully described in references cited in U.S. Pat. Nos. 6,001,861 and 6,114,326, incorporated herein by reference. According to the International RLS Study Group, these four minimal criteria already allow clinical diagnosis. RLS is considered by some to be a sleep disorder in which a person experiences unpleasant sensation in the legs described as creeping, tingling, pulling, or painful. One or both legs may be affected. The sensations occur when the person with RLS lies down or sits for prolonged periods of time, such as at a desk, riding in a car, or watching a movie. RLS symptoms worsen during periods of relaxation and decreased activity. The evening and night hours tend to be more troublesome for RLS sufferers.

Sensory and motor symptoms in RLS often result in severe sleep disturbances with prolonged sleep latency, decreased total sleep time with reduced or absent slow wave sleep and decreased sleep efficiency. RLS patients often sleep best toward the end of the night or during the morning hours. Because of less sleep at night, people with RLS may feel sleepy during the day on an occasional or regular basis. Almost all RLS patients present periodic leg movements (PLM) during sleep (PLMS) and also while being awake. The number of PLM and related parameters are considered to be a marker for the severity of RLS since PLM are frequently associated with nocturnal arousals or awakenings and if present during wakefulness may prevent patients from falling asleep. Therefore performing polysomnography is usually needed to evaluate the efficacy of drug therapies.

As a result of problems both in sleeping and while awake, people with RLS may have difficulties with their job, social life, and recreational activities. RLS is reasonably common and always distressing. In the past some have called it "Crazy Legs." RLS sensations have been described as pulling, drawing, crawling, wormy, boring, tingling, pins and needles, prickly and sometimes painful sensations that are usually accompanied by an overwhelming urge to move the legs. Sudden muscle jerks may occur.

Various agents have been used to treat RLS. While there have been reports of the use of a levodopa-based product called Restex® made by Roche Pharmaceuticals in Germany, no substance is currently approved in the U.S. for this indication.

Over the years, several treatments have been proposed for RLS. Typically treatments are grouped into four categories: anticonvulsant drugs, benzodiazepines, opioids and dopaminergic agents.

Anticonvulsants. Several anticonvulsant drugs have been tested for use in treating RLS. Anticonvulsants appear to work by decreasing sensory disturbances (the unpleasant sensations) and the urge to move. These drugs are particularly effective for some, but not all, patients with marked daytime symptoms, particularly people who have pain syndromes associated with their RLS. Gabapentin (Neurontin) is the anticonvulsant that has shown the promise in treating the symptoms of RLS. Possible side effects of gabapentin include dizziness, sleepiness, fatigue, increased appetite, and unsteadiness. The sedative properties of gabapentin may impair the ability to operate heavy machinery, including a motor vehicle.

Benzodiazepines. Several benzodiazepines, including clonazepam (Klonopin), nitrazepam, lorazepam and temazepam, have been used to treat RLS and sometimes improve the quality of nocturnal sleep. Benzodiazepines are central nervous system depressants that do not fully suppress RLS sensations or leg movements, but allow patients to obtain more sleep despite the problems. Some drugs in this group result in daytime drowsiness.

Opioids are narcotic analgesic (pain-killing) drugs and relaxing drugs that can suppress RLS and PLMS in some people especially those with severe and relentless symptoms of RLS. Some examples of medications in this category include codeine, propoxyphene (Darvon or Darvocet), oxycodone (Percocet, Tylox, Roxiprin), pentazocine (Talwin), hydrocodone (Vicodin), and methadone.

The therapeutic action of opioids was mentioned in the original description of RLS by Ekbom. Recently, this effect has been further documented in open clinical trials, see Trzepacz P T, Violette E J, Sateia M J (1984). Response to opioids in three patients with restless legs syndrome. *Am J. Psychiatry*; 141:993–99, and Hening W A, and periodic movements in sleep in restless legs syndrome; treatment with opioids. *Neurology*; 36:1363–1366 (1986). In these studies RLS was found to be reversible by naloxone, an opioid receptor antagonist. Opioids are potent suppressors of RLS and PLMS, but they carry the risk for abuse and the danger of addiction limit. Side effects and adverse reactions include dizziness, sedation, nausea, vomiting, constipation, hallucination, and headache. In severe cases, however, and especially in those undergoing hemodialysis, opiates may be an alternative treatment.

Dopaminergic drugs have produced some interesting results. Dopaminergic agents are drugs that are usually used to treat Parkinson's disease and in some cases may appear to provide some short term relief for some people with RLS. RLS is not a form of Parkinson's disease but is a distinct neurologic condition. Several studies have shown that L-dopa given with a peripheral carboxylase inhibitor at a 10:1 ratio is effective in treating RLS. See for example the following articles: Brodeur C, Montplaisir J, Marinier R, Godbout R., "Treatment of RLS and PMS with L-dopa: a double-blind controlled study," *Neurology*; 35:1845–1848 (1988). Montplaisir J, Godbout R, Poirier G, Bédard M. A., "Restless legs syndrome and periodic movements in sleep: physiopathology and treatment with L-dopa," *Clinical Neuropharmacology*; 9:456–463 (1986). Von Scheele C, "Levodopa in restless legs," *Lancet*; 2:426–427 (1986). Akpinar S., "Restless legs syndrome treatment with dopaminergic drugs," *Clinical Neuropharmacology*; 10:69–79 (1987).

A controlled study using polysomnography (PSG) recordings in a double-blind design also showed that L-dopa administered twice at night produces a significant reduction of RLS occurring at bedtime and of PLMS throughout the night. Brodeur C, Montplaisir J, Marinier R, Godbout R., "Treatment of RLS and PMS with L-dopa: a double-blind controlled study," Neurology; 35:1845–1848 (1988). In most cases, L-dopa 100 mg, in conjunction with the decarboxylase inhibitor carbidopa 10 mg, completely suppresses RLS although a rebound (augmentation) of PLMS is often observed in the last part of the night. Montplaisir J, Godbout R, Poirier G, Bédard M. A., Clinical Neuropharmacology; 9:456–463 (1986). The two major side effects frequently seen in patients treated with L-dopa are: 1) a rebound of symptoms during daytime when patients are only treated at night; and 2) a single dose of L-dopa at bedtime decreases PLMS in the first third of the night but induces a rebound of these movements in the last third of the night when L-dopa is no longer effective. Id. Similarly, the same study showed that when L-dopa treatment is repeated in the middle of the night, patients with severe cases may experience de novo paraesthesia and restlessness during the daytime.

Bromocriptine, a D2 receptor agonist, was also used in RLS treatment. Walters, A S; Hening, W A; Chokroverty, S; Gidro-Franck, S. A double blind randomized crossover trial of bromocriptine and placebo in restless leg syndrome. Ann Neurol; 1988 24:455–458. After a dose of 7.5 mg was administered 1 to 3 hours prior to sleep, 5 of 6 patients reported better subjective improvement in restlessness and paresthesia compared to placebo. Side effects reported were transient nasal stuffiness and lightheadedness in one patient.

Pergolide, the dopamine D1/D2 agonist, (half-life 7–16 hours) in combination with a low dose of L-dopa can lead to clinical improvement in patients who do not respond to L-dopa alone, but can also cause several important side effects such as orthostatic hypotension and gastrointestinal problems.

The Internet RLS site, http://www.rls.org, had the following to say about dopaminergic drug treatments. Note, the Internet site may be updated at any time, the following quotes were copied in March 1999. "The primary and first-line treatment for RLS is with dopaminergic agents, which work in the central nervous system by enhancing the levels of dopamine, a chemical that the body naturally produces and that regulates the delivery of messages between cells in the nervous system." But then the site provides this warning: "The dopaminergic agent that has been used most often is carbidopa-levodopa (Sinemet® DuPont-Merck). The advantages to using Sinemet® are that this drug has been available the longest and it is the least-expensive dopaminergic agent. However, Sinemet® does have one very important disadvantage: up to 85% of people who take this drug for the treatment of RLS develop a phenomenon known as augmentation." The site provides another description of augmentation. "What happens with augmentation is this: the usual dose of Sinemet® will allow you to obtain relief from your symptoms so that you will be able to sleep at night, but the sensations, the need to move, and the restlessness will develop (frequently with an increased intensity) earlier in the day (during the afternoon or even during the morning). If this happens, you may be tempted to increase your dose of Sinemet to treat these daytime symptoms, but that would be the wrong approach. If augmentation does develop, increasing your dosage of Sinemet® will only worsen rather than improve your symptoms. Most people with RLS who develop augmentation must switch to another medication."

"Though Sinemet® does work well for many people and has minimal side effects (primarily gastrointestinal discomfort, nausea, vomiting, and headache), every person who takes this drug for the treatment of RLS needs to clearly understand the potential for developing augmentation. One other consideration that you should understand is that because protein interferes with the absorption of Sinemet®, you should avoid consuming a high-protein meal just before taking this medication."

The Internet site continues and discusses other possible treatments.

"A newer drug, pergolide mesylate (Permax®), is showing great promise in treating RLS. Recent studies have shown that this medication is as effective as Sinemet® and has much less potential for causing augmentation (10% for Permax® vs. 80% for Sinemet®). The disadvantages of Permax® are that it is more expensive than Sinemet® and it has not been used as long, so that physicians are less familiar with prescribing this drug. The primary side effects are dizziness, nausea, and nasal congestion."

"Bromocriptine mesylate (Parlodel®) is another dopaminergic agent that is used to treat RLS. Results of studies regarding the effectiveness of bromocriptine are mixed, although individual patients have reported good results."

"Permax® and Parlodel® are both dopamine-receptor agonists, meaning that they work at the dopamine-binding site, while Sinemet® augments the body's normal production of dopamine. Other studies suggest that patients treated with Permax® (pergolide) will develop tolerance to the drug."

Considering the problems with all the possible treatments mentioned above, it is fair to say, there is no optimally effective treatment for RLS. An RLS patient who turns to the Internet and sees the above comments will be overwhelmed with possible treatments, such as, iron supplements, melatonin, Prozac®, Sinement®, Klonopin®, clonazepam, all the drug and drug catagories mentioned above and even electrical stimulation to the legs or feet before bedtime. See http://www.rls.org. On the Internet one can find the suggestion that there is no good treatment regime for RLS, that medical books will list over 15 different treatments or protocols but that none of them are very effective. The following quote from an RLS suffer is posted on the Internet RLS site. "I feel as if worms are creeping and crawling in my legs. I need to wiggle my legs to make the feelings go away. Sometimes, in the evening, when I'm driving or just sitting at the movies or watching TV, I want to keep moving my legs. I want to just hit them with a hammer." http://www.rls.org Currently a physician might be tempted to use levodopa in conjunction with a dopa decarboxylase inhibitor (DDCI) such as carbidopa. Controlled studies with levodopa have proven the beneficial effects on subjective RLS symptoms and sleep quality confirmed by polysomnographic studies. Since regular release formulas often do not maintain therapeutic coverage throughout the night, sustained release formulas are attempted. Although many RLS patients show an excellent response to levodopa, there is increasing evidence that the relatively short duration of action and augmentation of symptoms may be a limiting factor of levodopa therapy.

Fairly recent patent documents have suggested new treatments may be available and useful but they have not yet been widely prescribed, see U.S. Pat. No. 6,114,326 which discloses the use of Cabergoline, a synthetic ergoline derivative, and a dopamine agonist, either by itself or in combination with levodopa as a treatment for RLS. In U.S. Pat. No. 6,001,861, the use of pramipexole a dopamine $D_3/D_2$ agonist to treat RLS is disclosed.

Augmentation is described above, it comprises an earlier onset of RLS symptoms in the evening than before treatment, appearance of symptoms during the day, an involvement of other body parts (i.e. the arms) or an increased severity of symptoms. Considering the problem of augmentation, alternative treatment options for RLS are of major interest, especially for patients with severe RLS. The choice of where to turn for a possible treatment of RLS is a problem for any treating physician, with the possible known treatments presenting serious drawbacks. Here we present new compounds that may be used to treat RLS.

SUMMARY OF THE INVENTION

This invention provides methods for the treatment of restless legs syndrome (RLS) in a patient suffering from RLS with heterocyclic amines, substituted phenylazacycloalkanes, and the pharmaceutically acceptable salts thereof.

In one aspect the invention provides a method for the treatment of RLS in a patient suffering from RLS and in need of treatment, comprising administration of a heterocyclic amine of structural formula I:

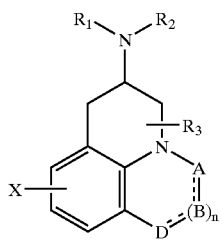

Formula I or pharmaceutically acceptable salts thereof, wherein:

$R_1$, $R_2$, and $R_3$ are independently
  a) hydrogen,
  b) $C_{1-6}$ alkyl, $C_{3-5}$ alkenyl, or $C_{3-5}$ alkynyl,
  c) $C_{3-7}$ cycloalkyl, $C_{4-10}$ cycloalkyl- or phenyl- substituted $C_{1-6}$ alkyl, or
  d) $R_1$ and $R_2$ are joined to form a $C_{3-7}$ cyclic amine which can contain additional heteroatoms and/or unsaturation;

X is
  a) hydrogen,
  b) $C_{1-6}$ alkyl,
  c) halogen,
  d) hydroxy,
  e) alkoxy, or
  f) cyano,
  g) carboxamide,
  h) carboxyl, or
  i) carboalkoxyl;

A is
  a) CH, $CH_2$, CH-halogen, $CHCH_3$, C=O, C=S, C—$SCH_3$, C=NH, C—$NH_2$, C—$NHCH_3$, C—$NHCOOCH_3$, or C—NHCN,
  b) $SO_2$, or
  c) N;

B is
  a) $CH_2$, CH, CH-halogen, or C=O,
  b) N, NH or N—$CH_3$, or
  c) O n is 0 or 1; and D is
  a) CH, $CH_2$, CH-halogen or C=O,
  b) O, or
  c) N, NH or N—$CH_3$.

Preferred compounds of formula I for the present invention include (R)-5,6-Dihydro-5-(methylamino)-4H-imidazo[4,5,1-ij]-quinolin-2(1H)-one, (5R)-5-(methylamino)-5,6-dihydro-4H-imidazo[4,5,1-ij]quinoline-2(1H)-thione, and the pharmaceutically acceptable salts of any said compound.

In another aspect the invention provides a method for the treatment of RLS in a patient suffering from RLS and in need of treatment, comprising the administration of a substituted phenylazacycloalkane of structural formula II:

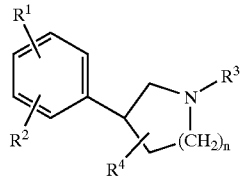

Formula II or a pharmaceutically acceptable salt thereof, wherein:
  n is 0–3;
  $R^1$ and $R^2$ are independently H (provided only one is H at the same time), —OH (provided $R^4$ is other than hydrogen), CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, $COR^4$, $COOR^4$, $CON(R^4)_2$, $SO_xCH_3$ (where, x is 0–2), $SO_xCF_3$, $O(CH_2)_x CF_3$, $SO_2N(R^4)_2$, CH=$NOR^4$, $COCOOR^4$, COCOON$(R^4)_2$, $C_{1-8}$ alkyls, $C_{3-8}$ cycloalkyls, $CH_2OR^4$, $CH_2(R^4)_2$, $NR^4SO_2CF_3$, $NO_2$, halogen, a phenyl at positions 2, 3 or 4, thienyl, furyl, pyrrole, oxazole, thiazole, N-pyrroline, triazole, tetrazole or pyridine;
  $R^3$ is hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ (where m is 1–8), $CH_2SCH_3$ or a $C_4$–$C_8$ alkyl bonded to said nitrogen and one of its adjacent carbon atoms inclusive to form a cyclic structure;
  $R^4$ is independently hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8;
  $R^5$ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$;
  $R^6$ and $R^7$ are independently hydrogen, $C_1$–$C_8$ alkyl, $C_3$–$C_8$ cycloalkyl, $C_4$–$C_9$ cycloalkylmethyl, $C_2$–$C_8$ alkenyl or $C_2$–$C_8$ alkynyl; and
  with the proviso that when $R_1$ is 2-CN or 4-CN, $R^2$ is H, $R^3$ is n-Pr and n is 1 or 3 then such compound is a pure enantiomer.

Preferred compounds of formula II for use in the present invention include the compound wherein $R^1$ is CN; the compound wherein $R^2$ is H and $R^3$ is n-propyl; the compound wherein $R^1$ is an —$OSO_2CF_3$; the compound wherein R1 is $SO^2CH_3$; the compound wherein $R^2$ is H and $R^3$ is a $C_{1-8}$ alkyl; the compound wherein n is 2; the compound wherein $R^1$ is 3-OH, $R^2$ is H, $R^3$ is n-propyl and $R^4$ is a $C_{1-8}$ alkyl; and the compound wherein n is 0.

Particularly preferred compounds of formula II include (3S)-3-[3-(methylsulfonyl)phenyl]-1-propylpiperidine hydrochloride, (3S)-3-[3-(methylsulfonyl)phenyl]-1-propylpiperidine hydrobromide, and (3S)-3-[3-(methylsulfonyl)phenyl]-1-propylpiperidine (2E)-2-butenedioate (1:1).

DETAILED DESCRIPTION OF THE INVENTION

The present invention provides methods and use of two classes of compounds having dopamine receptor activities for the treatment of RLS.

One class of compounds useful for treating RLS in the present invention are those compounds, or pharmaceutically acceptable salts thereof, disclosed generically or specifically in U.S. Pat. Nos. 5,273,975 and 5,436,240. These compounds are generically referred to as heterocyclic amines and are structurally represented by formula I, wherein:

$R_1$, $R_2$, and $R_3$ are independently
  a) hydrogen,
  b) $C_{1-6}$ alkyl, $C_{3-5}$ alkenyl, or $C_{3-5}$ alkynyl,
  c) $C_{3-7}$ cycloalkyl, $C_{4-10}$ cycloalkyl- or phenyl- substituted $C_{1-6}$ alkyl, or
  d) $R_1$ and $R_2$ are joined to form a $C_{3-7}$ cyclic amine which can contain additional heteroatoms and/or unsaturation;

X is
  a) hydrogen,
  b) $C_{1-6}$ alkyl,
  c) halogen,
  d) hydroxy,
  e) alkoxy,
  f) cyano,
  g) carboxamide,
  h) carboxyl, or
  i) carboalkoxyl;

A is
  a) CH, $CH_2$, CH-halogen, $CHCH_3$, C=O, C=S, C—$SCH_3$, C=NH, C—$NH_2$, C—$NHCH_3$, C—$NHCOOCH_3$, or C—NHCN;
  b) $SO_2$, or
  c) N;

B is
  a) $CH_2$, CH, CH-halogen, or C=O, or
  b) N, NH or N—$CH_3$,
  c) O;

n is 0 or 1; and

D is
  a) CH, $CH_2$, CH-halogen or C=O,
  b) O, or
  c) N, NH or N—$CH_3$.

Illustrative preferred compounds of formula I for use in the present invention include the compound wherein D is N or NH, and n is 0; the compound wherein A is CH, $CH_2$, $CHCH_3$, C=O, C=S, C—$SCH_3$, C=NH, C—$NH_2$, C—$NHCH_3$, C—$NHCOOCH_3$, or C—NHCN; and the compound wherein A is CH or C=O.

An especially suitable compound of formula I in the present invention is a compound of formula Ia,

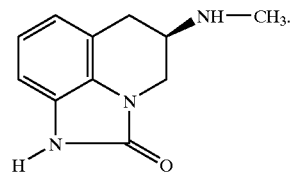

Formula Ia

The name of the compound of formula Ia is (R)-5,6-Dihydro-5-(methylamino)-4H-imidazo[4,5,1-ij]-quinolin-2(1H)-one (uninverted CAS name) or (5R)-5-(methylamino)-5,6-dihydro-4H-imidazo[4,5,1-ij]quinolin-2(1H)-one (Generated by ACD/Name software).

Another especially suitable compound of formula I in the present invention is the maleate salt of the compound of formula Ia, and is represented by formula Ib:

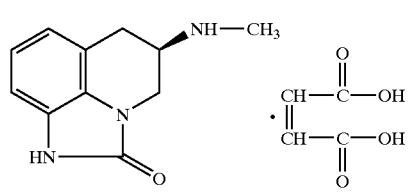

Formula Ib

The name of the compound of formula Ib is (R)-5,6-Dihydro-5-(methylamino)4H-imidazo[4,5,1-ij]-quinolin-2(1H)one (Z)-2-butenedioate (1:1) or (5R)-5-(methyamino)-5,6-dihydro-4H-imidazo[4,5,1-ij]quinolin-2(1H)-one maleate.

Another group of compounds within the generic Formula I shown above are selected heterocyclic amine compounds wherein A is C=S; the most preferred being, (5R)-5-(methylamino)-5,6-dihydro-4H-imidazo[4,5,1-ij]quinoline-2(1H)-thione, a compound of the formula Ic below, also referred to herein as the compound of formula VIII.

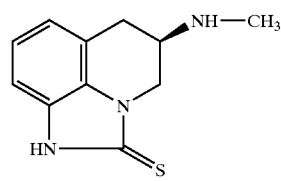

Formula Ic or Formula VIII and pharmaceutically acceptable salts thereof. It is preferred that (5R)-5-(methylamino)-5,6-dihydro-4H-imidazo[4,5,1-ij]quinoline-2(1H)-thione (IX) be present as a pharmaceutically acceptable salt. The pharmaceutically acceptable salts are preferred over the corresponding free amines since they are more water soluble and more crystalline. Pharmaceutically acceptable salts include salts of both inorganic and organic acids. The preferred pharmaceutically acceptable salts include salts of the following acids hydrochloric, hydrobromic, sulfuric, phosphoric, nitric, citric, methanesulfonic $CH_3$—$(CH_2)_{n1}$—COOH where $n_1$ is 0 thru 4, HOOC—$(CH_2)n_1$—COOH where n is as defined above, HOOC—CH=CH—COOH, φ—COOH. For other acceptable salts, see Int. *J. Pharm.*, 33, 201–217 (1986). It is more preferred that (5R)-5-(methylamino)-5,6-dihydro-4H-imidazo[4,5,1-ij]quinoline-2(1H)-thione be present as the maleate salt, which is (5R)-5-(methylamino)-5,6-dihydro- 4H-imidazo[4,5,1-ij]quinoline-2(1H)-thione maleate. The maleate salt is shown below as formula Id or formula IX.

Formula Id or IX

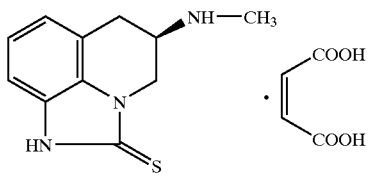

The heterocyclic amines, processes for making them, and methods for preparing medicaments from them are disclosed in U.S. Pat. Nos. 5,273,975 and 5,436,240, herein incorporated by reference. While U.S. Pat. No. 5,273,975 generically discloses and claims (5R)-5-(methylamino)-5,6-dihydro-4H-imidazo[4,5,1-ij ]quinoline-2(1H)-thione, it neither contains an example of nor specifically mentions this compound. (5R)-5-(methylamino)-5,6-dihydro-4H-imidazo[4,5,1-ij]quinoline-2(1H)-thione (VIII) is preferably made from the corresponding non-thio analog, (5R)-(methylamino)-5,6-dihydro-4H-imidao(4,5,1-ij)quinolin-(2H)-one (VII). A preferred process of making (5R)-(Methylamino)-5,6-dihydro-4H-imidao(4,5,1-ij)quinolin-(2H)-one (VII) is illustrated in PREPARATION 1 and EXAMPLEs 1–6, and is schematically shown in Chart A. A preferred method of transforming (5R)-(methylamino)-5,6-dihydro-4H-imidao(4,5,1-ij)quinolin-(2H)-one (VII) into (5R)-5-(methylamino)-5,6-dihydro-4H-imidazo[4,5,1-ij]quinoline-2(1H)-thione (VIII) is set forth in EXAMPLE 7. A preferred method of transforming (5R)-5-(methylamino)-5,6-dihydro-4H-imidazo[4,5,1-ij]quinoline-2(1H)-thione (VIII) into (5R)-5-(methylamino)-5,6-dihydro-4H-imidazo[4,5,1-ij]quinoline-2(1H)-thione maleate (IX) is set forth in EXAMPLE 8.

Another class of compounds useful in the present invention are those compounds, or pharmaceutically acceptable salts thereof, disclosed generically or specifically in U.S. Pat. Nos. 5,594,024 and 5, 462,947, both incorporated by reference herein. These compounds are generically referred to as substituted phenylazacycloalkanes and are structurally represented by formula II, wherein:

n is 0–3;

$R^1$ and $R^2$ are independently H (provided only one is H at the same time), —OH (provided $R^4$ is other than hydrogen), CN, $CH_2CN$, 2- or 4-$CF_3$, $CH_2CF_3$, $CH_2CHF_2$, CH=$CF_2$, $(CH_2)_2CF_3$, ethenyl, 2-propenyl, $OSO_2CH_3$, $OSO_2CF_3$, $SSO_2CF_3$, $COR^4$, $COOR^4$, CON$(R^4)_2$, $SO_xCH_3$ (where, x is 0–2), $SO_xCF_3$, $O(CH_2)_xCF_3$, $SO_2N(R^4)_2$, CH=$NOR^4$, $COCOOR^4$, COCOON$(R^4)_2$, $C_{1-8}$ alkyls, $C_{3-8}$ cycloalkyls, $CH_2OR^4$, $CH_2(R^4)_2$, $NR^4SO_2CF_3$, $NO_2$, halogen, a phenyl at positions 2, 3 or 4, thienyl, furyl, pyrrole, oxazole, thiazole, N-pyrroline, triazole, tetrazole or pyridine;

$R^3$ is hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ (where m is 1–8), $CH_2SCH_3$ or a $C_4$–$C_8$ alkyl bonded to said nitrogen and one of its adjacent carbon atoms inclusive to form a cyclic structure;

$R^4$ is independently hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8;

$R^5$ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$;

$R^6$ and $R^7$ are independently hydrogen, $C_1$–$C_8$ alkyl, $C_3$–$C_8$ cycloalkyl, $C_4$–$C_9$ cycloalkylmethyl, $C_2$–$C_8$ alkenyl or $C_2$–$C_8$ alkynyl; and with the proviso that when $R^1$ is 2-CN or 4-CN, $R^2$ is H, $R^3$ is n-Pr and n is 1 or 3 then such compound is a pure enantiomer.

Also useful in the present invention are the pharmaceutically acceptable salts of compounds of formula II above.

Preferred compounds of formula II for use in the present invention include: the compound wherein said $R^1$ is CN; the compound wherein $R^2$ is H and $R^3$ is n-propyl; the compound wherein said $R^1$ is an —$OSO_2CF_3$; the compound wherein R1 is $SO^2CH_3$; the compound wherein $R^2$ is H and $R^3$ is a $C_{1-8}$ alkyl; the compound wherein said n is 2; the compound wherein $R^1$ is 3-OH, $R^2$ is H, $R^3$ is n-propyl and $R^4$ is a $C_{1-8}$ alkyl; and the compound wherein n is 0.

A particularly suitable compound of formula II in the present invention is (3S)-3-[3-(methylsulfonyl)phenyl]-1-propylpiperidine hydrochloride (uninverted CAS name) or OSU 6162 or (3S)-3-[3-(methylsulfonyl)phenyl]-1-propylpiperidine hydrochloride (Generated by ACD/Name software), and is represented by formula IIa:

Formula IIa

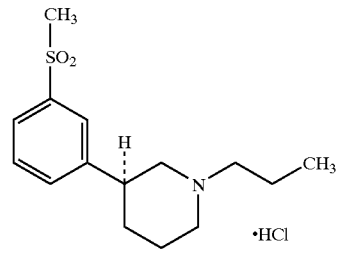

Another particularly suitable compound of formula II in the present invention is (3S)-3-[3-(Methylsulfonyl)phenyl]-1-propylpiperidine hydrobromide (uninverted CAS name) or (3S)-3-[3-(methylsulfonyl)phenyl]-1-propylpiperidine hydrobromide (Generated by ACD/Name software), and is represented by formula IIb:

Formula IIb

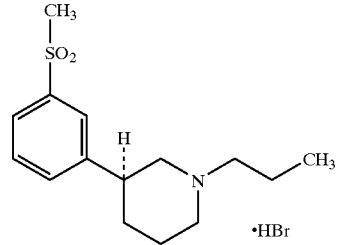

Yet another particularly suitable compound of formula II in the present invention is (3S)-3-[3-methylsulfonyl)phenyl]-1-propylpiperidine (2E)-2-butenedioate (1:1) (uninverted CAS name) or (S)-OSU6162, and is represented by formula IIc:

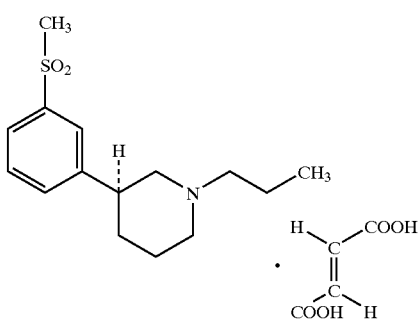

Formula IIc

The substituted phenylazacycloalkanes, processes for making them and methods for preparing medicaments from them are disclosed in U.S. Pat. Nos. 5,462,947 and 5,594,024, herein incorporated by reference.

Conventional pharmaceutical preparations of the heterocyclic amines and of the substituted phenylazacycloalkanes can be used, e.g., consisting essentially of an inert pharmaceutical carrier and an effective dose of the active substance; e.g., plain or coated tablets, capsules, lozenges, powders, solutions, suspensions, emulsions, syrups, suppositories, transdermal patch, etc. Tablets are preferred.

The effective dose range for the compounds of formula I is about 0.1 to 50 mg/day. More specifically, the effective dose range for compounds of Formula I wherein A is C=O is 1 to 50 mg/day, and often more than 1 mg will be administered to a patient per administration and per day, and preferably between 4 to 10 mg/day. For compounds of formula I wherein A is C=S, the effective dose range is 0.4 to 10 mg/day and often more than 0.4 will be administered to a patient per administration and per day, and preferably between 1.6 to 10 mg/day.

The effective dose range for the compounds of formula II is about 10 to 100 mg/day and often more than 10 mg will be administered to a patient per administration and per day, and preferably between 15 to 40 mg/day and most preferably 20 to 30 mg/day.

While the above dosage levels for the heterocyclic amines compounds and for the substituted phenylazacycloalkanes indicate mg/day, and typically they may be given once or twice a day, surprisingly, they may be given in these dosages on a less than daily basis. While the drugs may be given once a day or twice a day, they might only be given three times a week, two times a week or even once a week for some patients. For less than daily dosing the tablet size or amount of administration of drug can vary and the mg of drug administered per patient may in fact be the mg/day dose suggested above. When given on a daily or less frequent schedule, the daily dosages mentioned here would be given only for the day of administration.

Patients with milder forms of the disease would be expected to need less drug. Patients with more severe forms of the disease and those who have been treated with other dopaminergic agents may be expected to need more drug. Providing patients do not experience intolerable side effects, the dosage should be titrated to achieve a maximal therapeutic effect. Dosages should be increased gradually. The precise dosage for the heterocyclic amines compounds and for phenylazacycloalkanes would be determined by the treating physician evaluating such factors as the progression of the state of the disease, the weight and age of the patient, whether and what extent other drugs such as L-Dopa or levodopa were administered, and other such factors as are typically evaluated by a physician before determining the dosage of a CNS drug to be administered to a patient.

DEFINITIONS AND CONVENTIONS

The definitions and explanations below are for the terms as used throughout this entire document including both the specification and the claims.

DEFINITIONS

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm ($\delta$) downfield from TMS.

IR refers to infrared spectroscopy.

HPLC refers to high pressure liquid chromatography.

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

NMR refers to nuclear (proton) magnetic resonance spectroscopy, chemical shifts are reported in ppm ($\delta$) downfield from tetramethylsilane.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

RLS means Restless Legs Syndrome

Saline refers to an aqueous saturated sodium chloride solution.

Solubility of a solid in a solvent, the ratio of the solid to the solvent is weight/volume (wt/v).

Solvent pairs, the ratios of solvents used are volume/volume ratios (v/v).

Temperatures are in degrees Celsius.

TLC refers to thin-layer chromatography.

–$\phi$ refers to phenyl ($C_6H_5$).

$[\alpha]_D^{25}$ refers to the angle of rotation of plane polarized light (specific optical rotation) at 25° with the sodium D line (589A).

EXAMPLES

Without further elaboration, one skilled in the art can, using the preceding description, practice the present invention to its fullest extent. The following detailed examples and Chart A describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1 (R)-Naproxen Chloride

R-naproxen (*Can. J. Chem.*, 72(1), 142–5 (1994), 260 g), methylene chloride (3.33 kg) and DMF (8.2 ml) are added to a reactor. Oxalyl chloride (191.8 g) is slowly added to this mixture. After addition of the oxalyl chloride, the slurry is stirred at 5 to 10° and then slowly warmed to 20–25°. The resulting mixture is concentrated to remove the methylene chloride, branched octane is added to the concentrate and the mixture is again concentrated. More branched octane is added to the concentrate and the mixture is cooled to 0° and stirred to crystallize. The crystal slurry is filtered, the crystal cake is washed with octane and dried at 20–25° to obtain the title compound.

The filtrate from the first crop is concentrated, branched octane is added and the mixture is cooled and stirred to obtain a second crop of the title compound. The slurry is filtered, the crystal cake is washed with branched octane and dried at 20–25°.

EXAMPLE 1 1-Benzyl-4H-imidazo[4,5,1-ij]quinolin-2(1H)-one (II)

A mixture of 4H-imidazo[4,5,1-ij]quinolin-2(1H)-one (I, *J. Heterocyclic Chem.*, 19, 837–49 (1982), 1.0 g, 5.8mmol) in DMF (10 ml) is cooled to 0° and treated with potassium t-butoxide in THF (1.98 M, 3.2 ml, 6.3 mmol) maintaining the reaction temperature at 0°. The resulting mixture is stirred at 0° for 10 minutes. Benzyl bromide (0.73 ml, 6.1 mmol) is then added while maintaining the reaction temperature at 0°. After 1 hour, the mixture is partitioned with methyl t-butyl ether (MTBE) from water followed by several water washes. The MTBE phase is concentrated under reduced pressure. The concentrate is cooled to 0°, filtered and washed two times with 0° MTBE. The product is dried at 50° under reduced pressure with a nitrogen purge to give the title compound, CMR (CDCl$_3$, 100 MHz) 153.78, 136.44, 128.69, 127.67, 127.60, 126.73, 125.86, 122.90, 122.78, 121.28, 116.92, 116.17, 108.36, 44.95 and 42.37 δ.

EXAMPLE 2 (5R,6R)-1-Benzyl-5-bromo-6-hydroxy-5,6-dihydro-4H-imidazo[4,5,1-ij]quinolin-2(1H)-one (III)

1-Benzyl-4H-imidazo[4,5,1-ij]quinolin-2(1H)-one (II, EXAMPLE 1, 240 g), acetonitrile (1.086 kg), water (227 ml) and fluoboric acid (48.5%, 13.4 g) are mixed and cooled to 0 to 5°. Dibromantin (163.5 g) is slurried into acetonitrile and is added to the reaction mixture. The reaction is carried out for about 3 hr at 0 to 5°. After the reaction is complete, methyl t-butyl ether is added over about 45 minutes keeping the reaction temperature in the pot below 10°. The slurry is cooled to −10 to −15°, stirred for an hour and then filtered. The product is washed with precooled methyl t-butyl ether, dried with 40° nitrogen to give the title compound, CMR (CDCl$_3$) 156.0, 137.8, 130.5, 129.6, 129.3, 129.1, 126.6, 123.6, 122.5, 119.6, 110.4, 69.9, 49.6, 47.7, 46.9 and 43.8 δ.

EXAMPLE 3 (SS,6S)- 1-Benzyl-5-bromo-2-oxo-1,2,5,6-tetrahydro-4H-imidazo[4,5,1-ij]quinolin-6-yl (2R)-(6-methoxy-2-naphthyl)propanoate (IVA) and (5R,6R)-1-benzyl-5-bromo-2-oxo-1,2,5,6-tetrahydro-4H-imidazo[4,5,1-ij]quinolin-6-yl (2R)-(6-methoxy-2-naphthyl)propanoate (IVB)

(5R,6R)-1-Benzyl-5-bromo-6-hydroxy-5,6-dihydro-4H-imidazo[4,5,1-ij]quinolin-2(1H)-one (III, EXAMPLE 2, 143 g), methylene chloride (3,136 g), N-methyl morpholine (100.2 g) and 4-dimethylaminopyridine (497 mg) are added to the reactor and the mixture is cooled to 0 to 5°. (R)-Naproxen chloride (PREPARATION 1, 118.5 g) dissolved in methylene chloride (694 ml) is added to the reactor over about 1 hr and the mixture is stirred at 0 to 5° to complete the reaction. If necessary, additional naproxen chloride is added to complete the reaction. Potassium carbonate solution diluted with water is added to the mixture. The aqueous phase is extracted with methylene chloride and the combined methylene chloride phase is washed with water. The washed mixture is concentrated by vacuum distillation and solvent exchange with ethyl acetate is performed. The concentrate is cooled to −10° and stirred. The crystal slurry is filtered and the crystal cake is washed with precooled methyl t-butyl ether and dried at 50° to give the title compound in solid form, (5S,6S)-1-benzyl-5-bromo-2-oxo-1,2,5,6-tetrahydro-4H-imidazo[4,5,1-ij]quinolin-6-yl (2R)-2-(6-methoxy-2-naphthyl)propanoate (IVA), CMR (CDCl$_3$) δ 173.2, 157.8, 153.4, 136.1, 134.6, 133.7, 129.2, 128.8, 127.8, 127.8, 127.6, 127.2, 125.9, 125.9, 125.6, 121.5, 121.4, 119.1, 113.2, 109.0, 105, 105.6, 69.2, 55.3, 45.4, 45.2, 42.5, 41.7 and 18.3.

EXAMPLE 4 (5R,6R)-1-Benzyl-5-hydroxy-6-(methylamino)-5,6-dihydro-4H-imidazo[4,5,1-ij]quinolin-2(1H)-one (V)

(5S,6S)-1-Benzyl-5-bromo-2-oxo- 1,2,5,6-tetrahydro-4H-imidazo[4,5,1-ij]quinolin-6-yl (2R)-2-(6-methoxy-2-naphthyl)propanoate (IVA, EXAMPLE 3, 110 g) is slurried in acetonitrile (1,297 g). After adding aqueous methylamine (40 wt %, 327 g) the reaction is carried out for about 12 hr at about 30°. After the reaction is complete, the mixture is concentrated and ethyl acetate is added. Dilute hydrochloric acid is added to make the water-soluble salt of the title compound. The byproduct (R-naproxen methylamide impurity) is insoluble in water and stays in the ethyl acetate phase. Further extractions and washes are carried out for better separation of the (naproxen acetamide) impurity with minimum loss of the desired product. Then a sodium hydroxide solution is added to the aqueous phase and the hydrochloride salt of the title compound is converted to the free base. The free base is less soluble in water and is extracted into ethyl acetate. The product mixture is concentrated and solvent exchanged with ethyl acetate to remove water. Crystallization is performed by adding branched chain octane and cooling the mixture. The resulting slurry is filtered, washed and dried at 500 to give the title compound, CMR (CDCl$_3$) δ 153.7, 136.3, 128.7, 127.8, 127.7, 125.7, 121.3, 119.9, 118.6, 107.5, 66.2, 60.1, 45.1, 42.6 and 34.0.

EXAMPLE 5 (7aS,8aR)-4-Benzyl-8-methyl-7,7a,8,8a-tetrahydroazireno[2,3-c]imidazo[4,5,1-ij]quinolin-5(4H)-one (VI)

(5R,6R)-1-Benzyl-5-hydroxy-6-(methylamino)-5,6-dihydro-4H-imidazo[4,5,1-ij]quinolin-2(1H)-one (V, EXAMPLE 4, 70 g) and THF (1,389 g) is concentrated to remove any moisture by distillation as a precaution due to reactivity of n-butyllithium towards water. The mixture is cooled to about −10° and n-butyllithium is added to make the lithium salt of the starting material with formation of n-butane byproduct in an exothermic reaction. Benzenesulfonyl chloride is added slowly to make benzenesulfonate in an exothermic reaction. The reaction mixture is warmed to 20–25° to complete the reaction. Agueous potassium carbonate solution is added to scavenge the benzenesulfonic acid and the mixture is stirred to allow crystallization. Water is added to complete crystallization, the slurry is stirred, cooled and filtered. The crystal cake is washed with water followed by branched chain octane and dried at 40 to 50° to give the title compound, CMR (CDCl$_3$) δ 154.1, 136.3, 128.6, 127.9, 127.6, 124.3, 120.7, 119.7, 107.4, 46.7, 44.9, 40.7, 38.1 and 37.6.

EXAMPLE 6 (5R)-(Methylamino)-5,6-dihydro-4H-imidazo[4,5,1-ij]quinolin-2(1H)-one (VII)

A mixture of (7aS,8aR)4-benzyl-8-methyl-7,7a,8,8a-tetrahydroazireno[2,3-c]imidazo[4,5,1-ij]quinolin-5(4H)- one (VI, EXAMPLE 5, 40 g) t-amyl alcohol (42.4 g) and anhydrous ammonia (1,200 g) is treated with lithium at −33°. After the lithium addition is complete, the reaction mixture changes from a yellow slurry to a dark blue mixture. This dark blue mixture is stirred for 30–60 minutes and then quenched with the addition of water. The cooling water is removed from the condenser and the ammonia is allowed to evaporate. The residue is dissolved in methanol. This mixture is then concentrated to dryness to give the title compound, which is carried on directly to the next step without isolation.

EXAMPLE 7 (5R)-5-(Methylamino)-5,6-dihydro-4H-imidazo[4,5,1-ij]quinoline-2(1H)-thione (VIII)

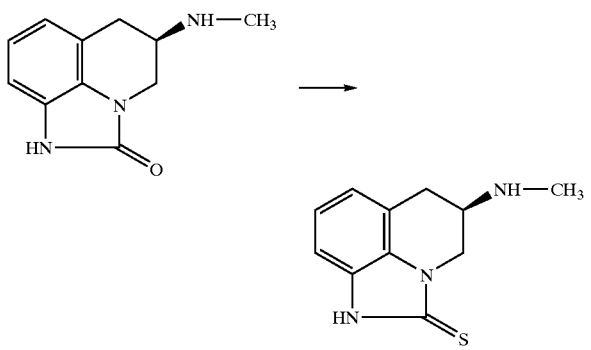

A mixture of (5R)-(methylamino)-5,6-dihydro-4H-imidazo[4,5,1-ij]quinolin-2(1H)-one (VII, EXAMPLE 6, 15.0 g, 73.8 mmol) and tetraphosphorus decasulfide (36.1 g, 81.2 mmol) in pyridine (300 mL) is heated in a 125° oil bath under nitrogen. The reaction is stirred for 5 hr. The mixture is cooled to 20–25° and the pyridine is removed under reduced pressure. Sodium hydroxide (2.2 N, 200 mL) is added and a vigorous reaction ensues. Additional sodium hydroxide (1 N) is added until a solution is formed. The solution is saturated with sodium chloride and extracted with methylene chloride (2.5 L, in portions). The organic phase is absorbed onto silicon dioxide (40 g) and purified via column chromatography (silicon dioxide, 225 g; methanol/methylene chloride, 3.5–5.0/96.5–95). The appropriate fractions are pooled and concentrated. The material is recrystallized from methanol/ethyl acetate/hexanes to give the title compound, mp=210–213°; IR (drift) 2940, 2907, 2884, 1483, 1458, 1391, 1366, 1354, 1254, 1239, 1229, 895, 762, 734 and 630 cm$^{-1}$; NMR (300 MHz, CDCl$_3$) δ 7.12, 7.03, 7.00, 4.30, 3.96, 3.30–3.50, 3.15, 2.88 and 2.57; MS (EI) m/z 219 (M$^+$), 190, 189, 187, 186, 164, 163, 155, 145; HRMS (FAB) calculated for C$_{11}$H$_{13}$N$_3$S (MH$^+$)=220.0908, found=220.0904.

EXAMPLE 8 (5R)-5-(Methylamino)-5,6-dihydro-4H-imidazo[4,5,1-ij]quinoline-2(1H)-thione maleate (IX)

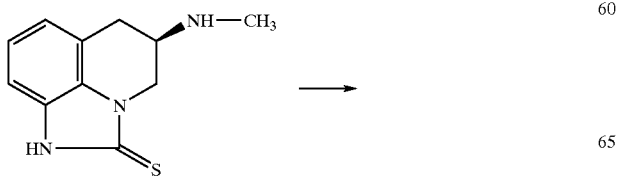

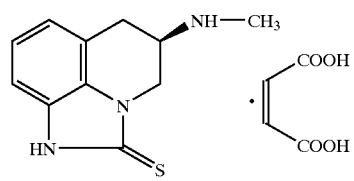

A solution of maleic acid (0.317 g, 2.36 mmol) in a minimal amount of methanol (~1 mL) is added to a mixture of (5R)-5-(methylamino)-5,6-dihydro-4H-imidazo[4,5,1-ij]quinoline-2(1H)-thione (VIII, EXAMPLE 7, 0.493 g, 2.25 mmol) in methylene chloride. The resulting solid is collected by filtration to give the title compound; mp=195–196°; [α]$^{25}$D=−60° (c 0.93, methanol); IR (drift) 3140, 3112. 3060, 2969, 1627, 1619, 1568, 1481, 1455, 1398, 1389, 1361, 1220, 868 and 747 cm$^{-1}$; NMR (300 MHz, CD$_3$OD) δ 7.20–7.30, 7.10–7.20, 6.26, 4.49, 4.31, 4.05–4.20, 3.28 and 2.83; CMR (100 MHz, DMSO-d$_6$+CD$_3$OD) δ 170.4, 169.4, 136.6, 131.1, 130.9, 125.1, 122.1, 116.2, 109.6, 53.9, 43.1, 31.9 and 27.2; MS (ESI) m/z=220.1 (MH$^+$).

CHART A

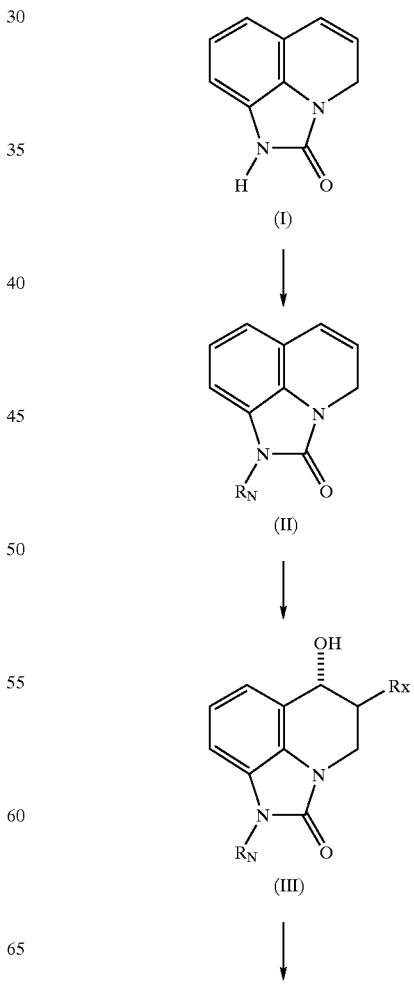

-continued

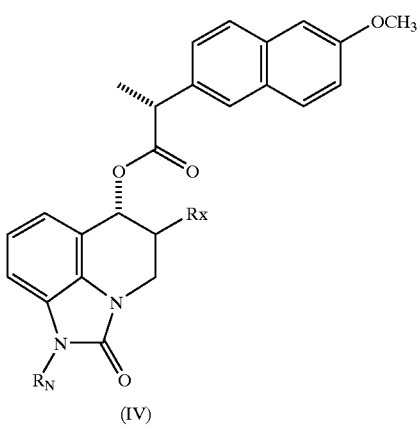

(IV)

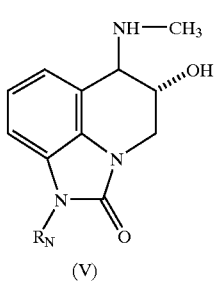

(V)

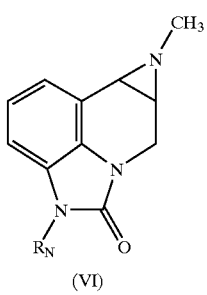

(VI)

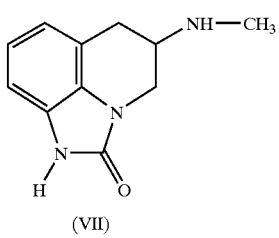

(VII)

-continued

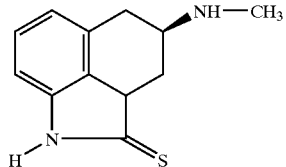

(VIII)

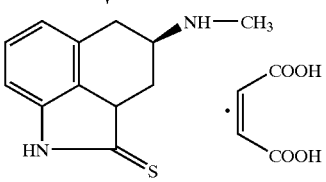

(IX)

wherein $R_{N1}$ is phenyl and Rx is bromo,

What is claimed is:

1. A method for treating restless legs syndrome in a patient suffering therefrom, comprising administration of an effective amount of a compound of formula II

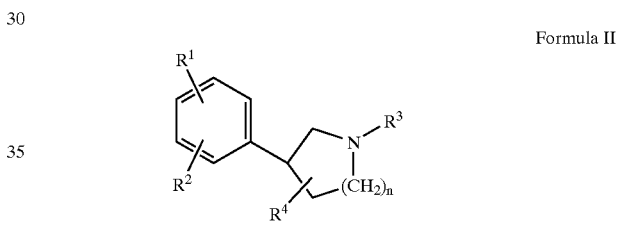

Formula II or a pharmaceutically acceptable salt thereof, wherein:

n is 0–3;

$R^1$ and $R^2$ are independently H (provided only one is H at the same time), —OH (provided $R^4$ is other than hydrogen), CN, $CH_2CN$, 2- or 4-$CF_3$, $CH_2CF_3$, $CH_2CHF_2$, $CH=CF_2$, $(CH_2)_2CF_3$, ethenyl, 2-propenyl, $OSO_2CH_3$, $OSO_2CF_3$, $SSO_2CF_3$, $COR^4$, $COOR^4$, $CON(R^4)_2$, $SO_xCH_3$ (where, x is 0–2), $SO_xCF_3$, $O(CH_2)_xCF_3$, $SO_2N(R^4)_2$, $CH=NOR^4$, $COCOOR^4$, $COCOON(R^4)_2$, $C_{1-8}$ alkyls, $C_{3-8}$ cycloalkyls, $CH_2OR^4$, $CH_2(R^4)_2$, $NR^4SO_2CF_3$, $NO_2$, halogen, a phenyl at positions 2, 3 or 4, thienyl, furyl, pyrrole, oxazole, thiazole, N-pyrroline, triazole, tetrazole or pyridine;

$R^3$ is hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ (where m is 1–8), $CH_2SCH_3$ or a $C_4$–$C_8$ alkyl bonded to said nitrogen and one of its adjacent carbon atoms inclusive to form a cyclic structure;

$R^4$ is independently hydrogen, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl, 3,3,3-trifluoropropyl, 4,4,4-trifluorobutyl, —$(CH_2)_m$—$R^5$ where m is 1–8;

R⁵ is phenyl, phenyl (substituted with a CN, $CF_3$, $CH_2CF_3$, $C_1$–$C_8$ alkyl, $C_3$–$C_8$ cycloalkyl, $C_4$–$C_9$ cycloalkyl-methyl, $C_2$–$C_8$ alkenyl, $C_2$–$C_8$ alkynyl), 2-thiophenyl, 3-thiophenyl, —$NR^6CONR^6R^7$, or —$CONR^6R^7$;

R⁶ and R⁷ are independently hydrogen, $C_1$–$C_8$ alkyl, $C_3$–$C_8$ cycloalkyl, $C_4$–$C_9$ cycloalkylmethyl, $C_2$–$C_8$ alkenyl or $C_2$–$C_8$ alkynyl; and with the proviso that when $R^1$ is 2-CN or 4-CN, $R^2$ is H, $R^3$ is n-Pr and n is 1 or 3 then such compound is a pure enantiomer.

2. The method of claim 1, wherein the dose of the compound is 10 to 100 mg/day.

3. The method of claim 1, wherein $R^1$ is CN.

4. The method of claim 1, wherein $R^2$ is H and $R^3$ is n-propyl.

5. The method of claim 1, wherein $R^1$ is —$OSO_2CF_3$.

6. The method of claim 1, wherein $R^1$ is —$SO_2CH_3$ and n is 2.

7. The method of claim 1, wherein $R^2$ is H and $R^3$ is a $C_{1-8}$ alkyl.

8. The method of claim 1, wherein n is 2.

9. The method of claim 1, wherein $R^1$ is 3-OH, $R^2$ is H, $R^3$ is n-propyl and $R^4$ is a $C_{1-8}$ alkyl.

10. The method of claim 1, wherein n is 0.

11. The method of claim 6, wherein the compound is (3S)-3-[3-(methylsulfonyl)phenyl-1-propylpiperdine or a pharmaceutically acceptable salt thereof.

12. A method of claim 11, wherein the compound is 3S)-3-[3-(methylsulfonyl)phenyl]-1-propylpiperidine hydrochloride.

13. The method of claim 12, wherein the dose of the compound is 10 to 100 mg/day.

14. The method of claim 12, wherein the dose of the compound is 20 to 30 mg/day.

15. A method of claim 11, wherein the compound is (3S)-3-[3-(methylsulfonyl)phenyl]-1-propylpiperidine hydrobromide.

16. The method of claim 11, wherein the compound used is, (3S)-3-[3-Methylsulfonyl)phenyl]-1-propylpiperidine (2E)-2-butenedioate (1:1).

* * * * *